(12) United States Patent
Francke et al.

(10) Patent No.: US 6,856,669 B2
(45) Date of Patent: Feb. 15, 2005

(54) METHOD AND APPARATUS FOR DETECTION OF IONIZING RADIATION

(75) Inventors: Tom Francke, Sollentuna (SE); Skiff Sokolov, Lidingö (SE)

(73) Assignee: XCounter AB, Danderyd (SE)

( * ) Notice: Subject to any disclaimer, the term of this patent is extended or adjusted under 35 U.S.C. 154(b) by 0 days.

(21) Appl. No.: 10/195,505

(22) Filed: Jul. 16, 2002

(65) Prior Publication Data

US 2003/0227996 A1 Dec. 11, 2003

(30) Foreign Application Priority Data

Jun. 7, 2002 (SE) .............................................. 0201742

(51) Int. Cl.$^7$ .......................................... G01N 23/201
(52) U.S. Cl. ...................................... 378/86; 250/374
(58) Field of Search .......................... 378/53–63, 86–90, 378/65; 250/374–379

(56) References Cited

U.S. PATENT DOCUMENTS

| 1,164,987 | A | | 12/1915 | Bucky |
|---|---|---|---|---|
| 4,611,341 | A | | 9/1986 | Brody |
| 4,864,594 | A | | 9/1989 | Inbar et al. |
| 4,995,068 | A | * | 2/1991 | Chou et al. ............... 378/189 |
| 5,090,040 | A | | 2/1992 | Lanza et al. |
| 5,247,560 | A | | 9/1993 | Hosokawa et al. |
| 5,352,896 | A | * | 10/1994 | Brown .......................... 250/368 |
| 5,649,997 | A | | 7/1997 | Cavallero et al. |
| 5,771,269 | A | | 6/1998 | Chao |
| 6,134,297 | A | | 10/2000 | Chao |
| 6,181,773 | B1 | | 1/2001 | Lee et al. |
| 6,385,282 | B1 | * | 5/2002 | Francke et al. ............... 378/51 |
| 6,493,424 | B2 | * | 12/2002 | Whitham ..................... 378/137 |

FOREIGN PATENT DOCUMENTS

EP      0398029 A1    11/1990

OTHER PUBLICATIONS

"Physics Of Radiology" Wolbarst, Appleton & Lange, 1993, p 104–106, 144, 220–221.*

* cited by examiner

*Primary Examiner*—Craig E. Church
(74) *Attorney, Agent, or Firm*—Harness, Dickey & Pierce, P.L.C.

(57) ABSTRACT

A method for detection of ionizing radiation comprises the steps of (i) directing ionizing radiation towards an object to be examined; (ii) preventing Compton scattered radiation, preferably at least 99% of the radiation Compton scattered in said object, from being detected; and (iii) detecting ionizing radiation spatially resolved as transmitted through said object to reveal a spatially resolved density of said object, wherein said ionizing radiation is provided within a spectral range such that more, preferably much more, photons of said ionizing radiation are Compton scattered than absorbed through the photoelectric effect in said object to thereby reduce the radiation dose to said object.

68 Claims, 2 Drawing Sheets

METHOD AND APPARATUS FOR DETECTION OF IONIZING RADIATION

FIELD OF THE INVENTION

The invention relates to a method and an apparatus for detection of ionizing radiation.

BACKGROUND OF THE INVENTION AND RELATED ART

Radiographic imaging detectors comprising an array of small sensors to capture a radiation-generated image are well known in the art. A collimated radiation beam is intensity modulated as it passes through a radiation-absorbing object and the transmitted beam as detected thus represents an inverted image of the absorption by the object, which in turn is related to the elemental composition, density, and thickness of the object.

The contrast and spatial resolution in captured X-ray images are deteriorated by X-rays scattered from the object being imaged. Anti-scatter grids or so-called Bucky grids, which absorb the scattered X-rays, while passing through the transmitted X-rays which have not interacted with the object, have been used extensively during a long period of time, see e.g. U.S. Pat. No. 1,164,987 issued to Bucky 1915, U.S. Pat. No. 6,181,773 B1 issued to Lee et al. 2001, and references therein. Typically, however, the Bucky grids are only capable of reducing the scatter to 30% or 20% of its total intensity. At the same time a Bucky grid also attenuates the undeflected transmitted X-rays.

Recently, more sophisticated approaches for reducing the amount of scattered X-rays have been developed using dual-detector or dual-energy methods, see U.S. Pat. No. 6,134,297 issued to Chao, and references therein.

Further, to improve contrast the broadband radiation from an X-ray tube is heavily filtered before being used for radiographic purposes. It is well known that at X-ray photon energies typically used, the photoelectric absorption is decreased as a power law as the X-ray photon energy increases, while the scattering is increased.

For soft tissue the photoelectric absorption is decreasing rapidly at energies above about 20 keV and this higher energy X-ray radiation does not contribute to the image recorded, but reduces the contrast in the image. Thus, higher energies are filtered out from the radiation. Of course, the elemental composition, density and thickness of the object determine the optimal choice of the photon energy.

Still further, lower energy X-ray radiation is almost completely absorbed in the tissue and thus does not contribute to the image as detected, but just adds to the radiation dose, to which the object is exposed. Thus, lower energies are also filtered out from the radiation and a narrowband radiation centered around 18 keV is typically employed for soft tissue applications such as e.g. mammography.

Finally, in all present X-ray detectors the efficiency to detect X-rays decreases rapidly with increasing X-ray energy. Furthermore, the position resolution decreases with increasing X-ray energy.

SUMMARY OF THE INVENTION

A problem with the known kind of approach is that most X-ray tubes have low efficiency at such low photon energy as 20 keV, i.e. the number of X-rays per unit power supplied to the tube is low.

Further, all X-ray tubes emit radiation within a wide energy spectrum. To create narrowband radiation, metallic foils filter the radiation from the X-ray tube, typically. This makes the energy spectrum narrow, but it also reduces the flux of X-rays within the selected narrowband. Thus, large load is put on the X-ray tube to obtain a reasonable radiation flux downstream the filters. Also, the relatively low flux affects the exposure time in an adverse manner, i.e. makes it long, which obviously limits the applicability of the technique.

The strong energy dependence E of the photoelectric absorption attenuation coefficient $\mu_{PE}$ results in an undesired narrow dynamic range of the object suitable for X-ray imaging. The transmission of X-rays through the object is given by the expression $$\text{Transmission} = \exp(\mu_{PE}(E, Z) * \rho * t)$$

where $\mu_{PE}$ is the photoelectric absorption coefficient of the material examined, $\rho$ is the density of the material and t is the thickness of the material. As the transmission depends exponentially on the product $\mu * \rho * t$, X-ray imaging is only suitable for objects where the product varies to a limited extent over the object to be imaged. Too large variations in the product results in that areas, where the product is significantly larger than the average, are underexposed and areas, where the product is significantly smaller than the average, are overexposed. The absorption coefficient of photoelectric absorption $\mu_{PE}$ depends also strongly on the atomic number Z of the material being examined, normally to a power law $Z^{2-3}$. Hence, small variation in the elemental composition of the object changes the product $\mu * \rho * t$ significantly and causes some areas of the image to easily be under- or overexposed.

The thick filters presently used between the X-ray tube and the object to be examined cause a lot of scattered X-rays, which are transmitted through the object and smear the X-ray image.

Another issue of high importance when designing radiographic imaging detectors is the radiation dose to the patient. While the development of efficient collimators, appropriate filters, and sensitive detector arrays during the last decades have effectively reduced the dose to the patient, still there is much to do. Further reduction of the radiation dose is a driving mechanism in detector design of today.

A main object of the invention is therefore to provide a method and an apparatus for detection of ionizing radiation, which overcome the above-identified problems as being related with the prior art.

In this respect there is a particular object to provide such a method and such an apparatus, which provide for only small amounts of energy deposited in an object to be detected.

A further object of the invention is to provide such a method and such an apparatus, which provide for the possibility of using broadband radiation for the measurement.

A still further object of the invention is to provide such a method and such an apparatus, wherein radiation in a spectral range is used, in which the risk of under- or over exposing some areas of the image is reduced.

Yet a further object of the invention is to provide such a method and such an apparatus, wherein X-rays over a wide energy range, and especially at high X-ray energies, can be detected with high efficiency.

A further object of the invention is to provide a detector for which the position resolution does not decrease at high X-ray energies.

These objects, among others, are attained by methods and apparatuses as claimed in the appended claims.

The inventors have found that by preventing Compton scattered radiation from being detected, and by providing ionizing radiation within a spectral range such that more, preferably much more photons, of the ionizing radiation are Compton scattered than absorbed through the photoelectric effect in said object, an entirely new field of radiology opens up. Since the probability of scattering is essentially the same for a broad spectrum of X-ray energies, broadband radiation including higher energies from the X-ray source can be used for the detection.

Further, the energy dependence on the absorption process in a material has not to be considered if the photoelectric absorption is negligible, or at least very low.

Besides, a scattered X-ray photon deposits only a fraction of its energy in a patient, whereas a photoelectrically absorbed X-ray photon deposits all its energy. Hence, to utilize scattered X-rays instead of photoelectrically absorbed X-rays for imaging, the dose to the patient is reduced.

A further advantage of the present invention is that if broadband radiation is used for the detection, there is less need of thick filters, the efficiency of the X-ray tube is increased, the load on the X-ray tube can be lowered, and the exposure time can be reduced (due to the higher X-ray photon flux).

A still further advantage is that if the photon energies employed are high enough such that variations in the image captured originate essentially only from Compton scattering in the object, these variations are due to the density of the object only, provided that the object thickness is constant, or known and corrected for. This is true since the attenuation coefficient for Compton scattering at photon energies of 10–300 keV is only weakly dependent on atomic number and photon energy. This is in sharp contrast to photoelectric absorption, which is heavily dependent on energy, and particularly on atomic number.

A yet further advantage of the present invention is that the X-ray image obtained is a shadow image of the density variations in the object. This image can be combined with a conventional X-ray image, which illustrates a combination of density and elemental composition (Z) variations in the object. From the two images a third image may be deduced illustrating only the elemental composition (Z) of the object.

Preventing Compton scattered radiation from being detected may be performed by means of a one-dimensional gas ionization detector including two electrodes, between which an ionizable gas is located, and a radiation entrance arranged such that said ionizing radiation enters said detector sideways between the electrodes, and electrons liberated by interaction between the ionizing radiation and the gas are accelerated in a direction essentially perpendicular thereto, wherein the distance between the electrodes is kept short to essentially only allow radiation collimated in a plane between the electrodes to ionize said gas. The distance between the electrodes may be below about 2 mm, preferably below about 1 mm, more preferably below about 0.5 mm, and most preferably between about 0.1 mm and 0.5 mm. The electrodes may be 1–50 cm, and preferably 3–10 cm, deep (in the direction of the incoming X-ray radiation).

The applicant has recently begun to verify the invention experimentally and good contrast has been observed using a wide X-ray spectrum of high energy X-rays, at which conditions a conventional detector system would not be capable to see any structure at all. It is believed that the above-described one-dimensional gas ionization detector discriminates more than 99% of the scattered photons; and by proper design it is assumed that about 99.9% or more of the scattered photons can be prevented from being detected.

Furthermore, the invention can be used at still higher photon energies where pair production occurs with many of the advantages identified above preserved. Such high-energy detection may be used for non-destructive testing of material in a variety of fields, as well as in medical applications, e.g. in oncology.

Further characteristics of the invention, and advantages thereof, will be evident from the detailed description of preferred embodiments of the present invention given hereinafter and the accompanying FIGS. 1–5, which are given by way of illustration only, and thus are not limitative of the present invention.

DESCRIPTION OF PREFERRED EMBODIMENTS

Figure 1:
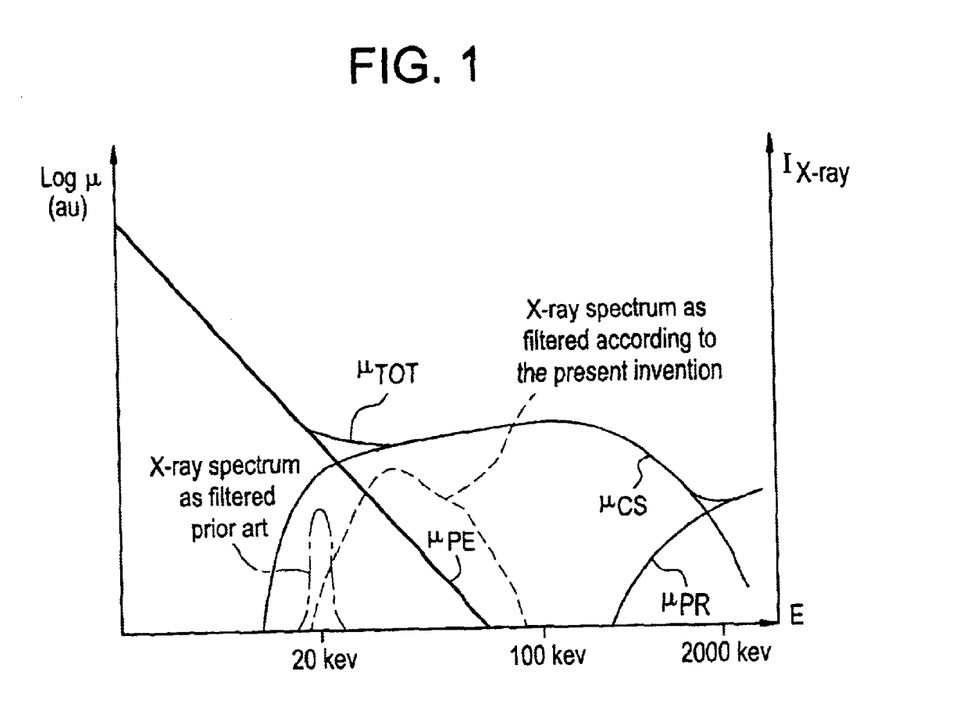
FIG. 1 is a schematic diagram illustrating photoelectric absorption, Compton scattering, pair production and total attenuation coefficients for human tissue as a function of X-ray photon energy; and a continuous X-ray spectrum of a typical X-ray source for use in the present invention.

As can be seen in FIG. 1, which is a schematic diagram illustrating photoelectric absorption, Compton scattering, pair production and total attenuation coefficient $\mu_{PE}$, $\mu_{CS}$, $\mu_{PR}$, $\mu_{TOT}$, for human soft tissue as a function of X-ray photon energy E, the photoelectric attenuation coefficient $\mu_{PE}$ decreases as a power law with photon energy, and at about 25 keV the Compton scattering attenuation coefficient $\mu_{CS}$ is comparable with the photoelectric absorption attenuation coefficient $\mu_{PE}$. Between about 30 and several hundred keV the Compton scattering attenuation coefficient $\mu_{CS}$ is completely dominating, whereas at higher photon energies (in the order of 1 MeV) the probability for pair production is increasing rapidly, and becomes the dominating interaction process. Further, it is noted that the Compton scattering attenuation coefficient $\mu_{CS}$ is almost constant between photon energies about 30 and several hundred keV. While FIG. 1 is illustrating an example only for human soft tissue, the relative overall structure of the diagram holds for a large variety of matter.

In FIG. 1 are also illustrated a typical continuous X-ray spectrum from an 30 kV wolfram-based X-ray tube as filtered by a rhodium filter according to prior art (dash-dotted line) for use in e.g. mammography examinations, as well as an X-ray spectrum from an 80 kV wolfram-based X-ray tube as filtered with an iron filter for the same application, but according to the present invention (dashed line). The prior art filtered spectrum is narrow due to requirements on the contrast in the image to be recorded and the strongly energy dependent photoelectric absorption. The inventive filtered spectrum, being broadband and displaced towards higher photon energies, will be discussed further below.

Figure 2:
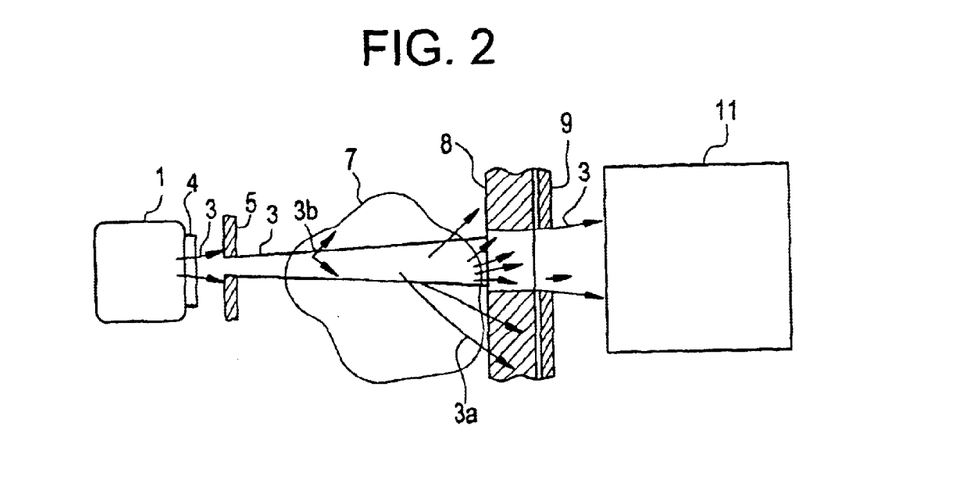
FIG. 2 illustrates schematically, in a side elevation view, an apparatus for radiography according to a general embodiment of the present invention.

FIG. 2 illustrates schematically, in a side elevation view, an apparatus for radiography according to a general embodiment of the present invention. The apparatus comprises, as seen from left to right, an X-ray source 1, a filter arrangement 4, a source aperture 5, an anti-scatter device 8 (which is optional), a detector aperture 9, (which also is optional), and a detector device 11.

The X-ray source emits an X-ray radiation beam within a wide energy spectrum. The beam is filtered by means of the filter arrangement at the output of the X-ray source 1. The filter arrangement 4 differs from a conventional filter in the sense that it transmits higher energies, and preferably a much wider spectrum, such as e.g. the one illustrated in FIG. 1. The radiation beam as filtered is subsequently passed through the optional source aperture 5 to collimate the beam. Preferably, the shape and size of the source aperture 5 is adapted to the particular size and kind of detector device 11. Thus, given a one-dimensional detector device, the aperture 5 is designed with a slit-shaped radiation transparent window, and given a rectangular two-dimensional detector device, the aperture 5 is preferably designed with a rectangular radiation transparent window.

The source collimator is optional and is used to reduce the dose to the patient, by producing a fan shaped beam of X-rays, which only illuminate the sensitive areas of the detector device 11. In applications where dose to the object is not an issue, e.g. in industrial applications, the aperture 5 can be omitted.

The radiation beam 3 as filtered and optionally collimated enters an object region, where an object 7 to be imaged is located. In the object 7 some photons may be photoelectrically absorbed, some may be Raleigh and Compton scattered (indicated by rays 3a in FIG. 1), and some photons may be converted into electrons and positrons in a pair production process, where these electrons and positrons may give rise to emission of X-ray photons (indicated by rays 3b in FIG. 1). The various processes depend on elemental composition, density and thickness of the object 7 and on the energy of the incident radiation beam 3.

The radiation beam transmitted through the object 7 without being deflected is passed through the optional anti-scatter device 8 and the optional detector aperture 9, and is subsequently detected by the detector device 11, while the scattered radiation is prevented from being detected. Typically, however, small amounts scattered radiation may be entered into the detector device 11 and blur the image recorded.

According to the present invention the filter arrangement 4 is adapted to the elemental composition, density and thickness of the object 7 to be imaged in a manner so the radiation beam as filtered is within a spectral range such that more photons of the radiation beam as filtered are Compton scattered than absorbed through the photoelectric effect in the object 7.

In the case of human soft tissue, such as breast tissue, the filtered radiation may be broadband X-ray radiation between 10 and 300 keV (i.e. similar to the broadband radiation spectrum of FIG. 1), preferably between 20 and 100 keV, and more preferably above 30 keV.

In other instances the filtered radiation is radiation above 30 keV.

Preferably, the filtered radiation is in a spectral range such that at least 2 times, more preferably at least 5 times, and most preferably at least 10 times more photons of the filtered radiation are Compton scattered than absorbed through the photoelectric effect in the object 7.

If possible the filtered radiation should be in a spectral range, at which photoelectric absorption does not essentially occur in the object 7.

By means of primarily using the amount of scattered, particularly Compton scattered, radiation instead of photoelectrically absorbed radiation as signal-affecting source for the image recorded, a number of advantages arise.

- Since the radiation is primarily scattered off the object 7 and not absorbed in it, the radiation dose to the object is reduced. At photon energies of 50 keV a Compton scattered photon deposits only about 10% of the energy compared to a photoelectrically absorbed photon.
- The filters may be made thinner since the radiation has not to be that heavily filtered (due to the Compton scattering attenuation coefficient compared to the photoelectric absorption attenuation coefficient).
- Less radiation is scattered in a thin filter than in a thick filter, which means that the scattered radiation from the filter arrangement 4 is reduced as compared with a conventional filter arrangement.
- The efficiency of the X-ray tube is increased since larger portions of the emitted spectrum are usable. This means also that the load on the X-ray tube can be lowered.
- The exposure time can be reduced due to the higher X-ray photon flux obtainable.
- The attenuation coefficient for Compton scattering at photon energies of 10–300 keV is only weakly dependent on atomic number and photon energy, and thus variations in the image captured are essentially due to variations in the density of the object only, provided that the object thickness is constant, or known and corrected for.

The latter property may be used in combination with a conventional detector to produce an image illustrating essentially only the elemental composition of the object provided that the thickness of the object is known. A first X-ray image, which illustrates essentially only density variations of the object, is produced from the amount of scattered, particularly Compton scattered, radiation as described above, whereas a second X-ray image, which is conventional and illustrates a combination of density and elemental composition variations of the object, is provided by any known technique. Finally, a third X-ray image illustrating essentially only the elemental composition of the object is constructed from the first and second X-ray images.

In a prior art device, where the image is produced mainly by photoelectric absorption in the object 7, the transmission through the object 7 is given by:

$$T_{PE}=\exp(\mu_{PE}(E, Z)*\rho*t)$$

where $\mu_{PE}$ is the photoelectric absorption coefficient of the material examined, $\rho$ is the density of the material and t is the thickness of the material.

By definition, the transmission $T_{PE}$ of the object 11 is given by:

$$T_{PE}=\#\gamma_{OUT-PE}/\#\gamma_{IN-PE}$$

where $\#\gamma_{IN-PE}$ is the number of X-rays entering the object at a specific position and $\#\gamma_{OUT-PE}$ is the number of X-rays transmitted through the object without being photoelectrically absorbed. $\#\gamma_{OUT-PE}$ is proportional to the number of photons $\#\gamma_{DET-PE}$ detected in the prior art detector (after correction for energy dependent detector efficiencies and possible energy dependent signal strength in the detector).

In a similar way, in the present invention where the image is produced mainly by Compton scattering in the object 7, the transmission through the object 7 is given by:

$$T_{CS}=\exp(\mu_{CS}*\rho*t)$$

where $\mu_{CS}$ is the Compton scattering attenuation coefficient of the material examined.

In a similar way, the transmission $T_{CS}$ of the object 11 is given by:

$$T_{CS} \# \gamma_{OUT-CS} / \# \gamma_{IN-CS}$$

where $\#\gamma_{IN-CS}$ is the number of X-rays entering the object at a specific position and $\#\gamma_{OUT-CS}$ is the number of X-rays transmitted through the object without being Compton scattered. $\#\gamma_{OUT-CS}$ is proportional to the number of photons $\#\gamma_{DET-CS}$ detected in the detector 11 (after correction for energy dependent detector efficiencies and possible energy dependent signal strength in the detector).

The elemental composition of each position of the object 7 may hence be determined as described above by combining the signal (pixel by pixel) in each image. In an alternative embodiment of the invention, the filter arrangement 4 has a filter function depending on the object 7 to be imaged such that the radiation 3 as filtered is within a spectral range such that more photons are converted to electrons and positrons in a pair production process than absorbed through the photoelectric effect in the object 7; and the detector device 11 is arranged to prevent radiation originating from pair production in the object 7 from being detected. Such high-energy detection may be used for non-destructive testing of material in a variety of fields, as well as in the medical field in e.g. oncology.

In order for the invention to work properly, the scattered radiation has to be discriminated from being detected to an especially large extent. Preferably at least 90%, more preferably at least 99%, and most preferably at least 99.9% of the Compton scattered radiation in the object 7 is prevented from being detected.

The present inventors have recently developed a detector device that fulfills this requirement, which will be described below with reference to FIGS. 3–4.

The detector device 11 is oriented such that the X-ray beam 3, which here is a planar radiation beam, can enter sideways between and parallel with a cathode 23 and an anode 24. An optional slit-shaped aperture 9 and a radiation transparent window 21 are provided at the front of the detector device 11 to form an entrance for the X-ray beam 3 to the detector device 11. The slit-shaped aperture 9 may be a thin metallic foil of e.g. tungsten, in which a thin slit is etched or cut; and the radiation transparent window 21 may be a thin plastic or carbon fiber foil.

Preferably, the electrodes 23, 24 and the window 21 define together with sidewalls a gas-tight confinement 25 capable of being filled with an ionizable gas or gas mixture. Alternatively, the electrodes 23, 24 are arranged within an external gas-tight casing (not illustrated). The ionizable gas or gas mixture may e.g. comprise krypton and carbon dioxide or xenon and carbon dioxide under pressure, preferably in a range of 1–20 atm.

A high voltage DC supply unit (not illustrated in FIGS. 3–4) is provided for the purpose of holding the cathode 23 and the anode 24 at suitable electric potentials to create an electric field within the inter-electrode confinement 25 for drift, and optionally electron avalanche amplification, of electrons and correspondingly produced positive ions therein.

Still further, the detector device 11 comprises a readout arrangement for detection of electrons drifted towards the anode 24 and/or the positive ions drifted towards the cathode 23. The readout arrangement is comprised of the anode 24 itself as illustrated in FIGS. 3–4. Alternatively, a separate readout arrangement may be arranged adjacent anode 24 or adjacent cathode 23, or elsewhere.

To provide for one-dimensional imaging capabilities, the anode/readout layer 24 is comprised of an array of conductive or semiconducting elements or strips 26 arranged side by side and electrically insulated from each other. To compensate for parallax errors in detected images the anode/readout strips 26 extend essentially in directions parallel to the direction of incident photons of the X-ray beam at each location. Thus, given a divergent beam from a point source the anode/readout strips 26 are arranged in a fan-like configuration. Each of the anode/readout strips 26 is preferably connected to a readout and signal-processing device (not illustrated in FIGS. 3–4), whereupon the signals from each strip can be processed separately. As the strips 26 also constitute the anode 24 suitable couplings for separation are needed.

Figure 3:
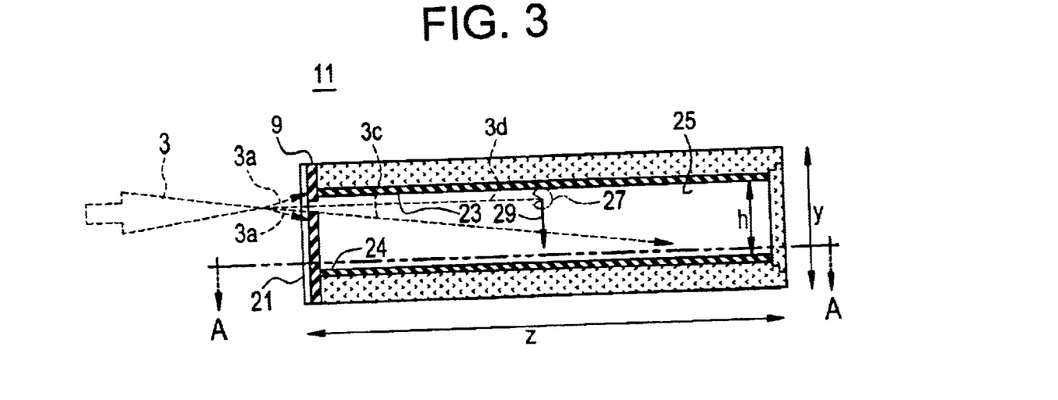
FIG. 3 illustrates schematically, in a cross-sectional side view, an embodiment of a detector device for use in the present invention.
Figure 4:
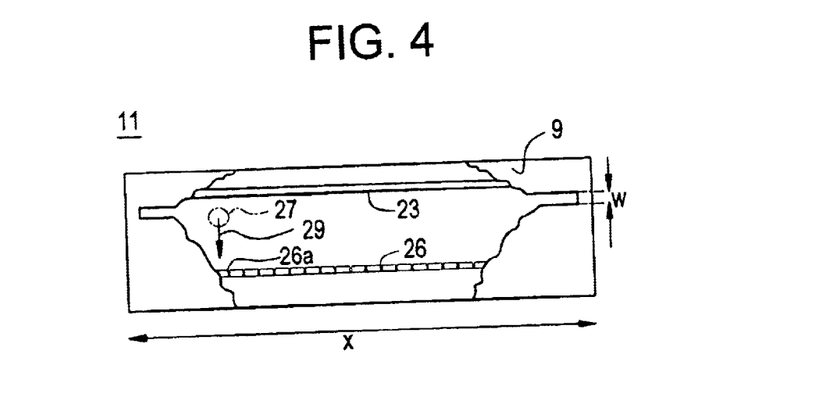
FIG. 4 illustrates schematically, in a front view with an entrance aperture partly removed, the detector of FIG. 3.

It shall be appreciated that the distance between the electrodes 23, 24 is strongly exaggerated in FIGS. 3–4 for illustrative purposes. As an example geometry the detector device may have a width x of about 40 mm, a thickness y of about 2 mm and a depth z of about 35 mm.

The distance h between the electrodes 23, 24 shall preferably be short to essentially only allow radiation collimated in a plane between the electrodes to ionize the gas. Thus, the distance h between the electrodes is kept at least 10 times, preferably at least 25 times, and most preferably 100 times, shorter than the depth z of the electrodes in the direction of the ionizing radiation as entered. Particularly, the distance h may be shorter than about 2 mm, preferably shorter than about 1 mm, more preferably shorter than about 0.5 mm, and most preferably between about 0.1 mm and 0.5 mm.

The width w of the aperture slit 9, which governs the thickness of the sheet of radiation that enters the detector device 11, may be as small as 10 $\mu$m or as wide as 2 mm. The aperture may alternatively be completely removed. Each readout strip 26 may be 10 $\mu$m–2 mm wide, which implies that several hundred or thousand strips may be arranged side by side in a single detector device, i.e. much more than illustrated.

In operation, X-rays enter the detector device 11 through the aperture slit 9, parallel and preferably close to the cathode 23. The X-rays will interact with the gas in the detector device 11 according to an exponential probability distribution where the majority of the X-rays convert early in the gas volume. The average interaction length may typically be 10–100 mm.

At an interaction, an X-ray photon 3d may transmit all or some of its energy to an electron in a gas atom, which travels through the gas and collides with new gas atoms, thereby liberating more electrons. In this process a cloud 27 typically of about thousand electrons is created. These electrons are attracted towards the anode in a direction 29 (vertical in FIGS. 3–4) due to the electric field applied, which direction is essentially perpendicular to the incoming X-ray photon trajectory. If the electric field applied is strong enough, gaseous-based electron avalanche amplification occurs. As the now large number of electrons approaches the anode, they induce electric signals in the strip 26a nearest to the cloud 27.

The electronic signal is detected by the readout electronics connected to the strip. In the electronics, the signal is amplified and compared with a threshold voltage. If the signal exceeds the threshold voltage, a counter specific for this strip is activated and adds one to a previous value stored. In this way, the number of X-rays impinging above each anode strip is counted. The method is called photon counting. Alternatively, the signals from many X-rays may be integrated into a single number related to the total energy deposited by all the X-rays together.

The X-ray scattered photons 3a are prevented from entering the detector device 11 by means of the aperture 9, and the scattered X-ray photons 3c that do enter the detector device 11, but are geometrically discriminated by the electrodes 23, 24 themselves or are at least not contributing to signals obtained to any important extent. In fact, provided that the detector device 11 are run in avalanche amplification mode, the signals in the readout elements 26 originate essentially only from ionization within a thin layer closest to the cathode 23, which may be at least 2–5 times thinner than the inter-electrode distance. This advantageous behavior is obtained as the amplification is exponential and electrons liberated closer to the anode 24 will not be able to produce signals strong enough to be detected.

In an alternative version of the detector device 11 the aperture 9 is replaced by, or combined with, a slit-shaped collimator or other kind of anti-scatter device 8 (not illustrated). The collimator may be similar to the aperture 9, but much deeper, in the direction of the incoming X-ray flux, to effectively collimate the radiation beam 3 and further reduce the amount of scattered radiation entered into the detector device 11. In order to efficiently reduce the scattered radiation also in the plane of the planar radiation beam 3 as entered into the detector device 11, the collimator 8 may be provided as a lamella or one-dimensional grid structure, which will let through a row of collimated beamlets. Preferably, the collimator is arranged with respect to the anode/readout strips 26 such that each beamlet will travel parallel and directly above a respective one of the anode/readout strips 26. Thus, given a divergent beam from e.g. a point source the collimator is adapted to produce a fan-like configuration of beamlets.

The gaseous detector can be made efficient, i.e. to have a high probability of detecting X-rays that are interacting in the gas, by using a gas with high atomic number (e.g. krypton, xenon or radon) and/or by pressurizing the gas and/or by making the detector very deep (in the direction of the incoming X-ray flux).

In prior art X-ray detectors, the signal that is detected originates from X-ray photons that interact with the conversion medium (the gas) through photoelectric effect and release all their energy to photoelectrons, which further ionize the medium. As the photoelectric absorption probability decreases rapidly with increasing X-ray energies, the efficiency of prior art detectors decreases rapidly with increasing X-ray energies.

Signals originating from X-rays which have Compton scattered in the conversion medium are not detected as the scattered X-rays carry most of the energy of the incoming X-rays (about 90% at 50 keV) and normally leave the conversion medium. The recoil electrons have too low energy, compared to the noise level in the detector, to be detected.

In a gaseous detector with avalanche amplification, as described above, the noise level in the detector is very low; and the recoil electrons (and the few electrons they can ionize) are amplified to a high degree in the avalanche amplification process. This makes it possible to detect the recoil electrons from Compton scattering in the conversion gas in the detector.

Since the attenuation coefficient for Compton scattering does not decrease significantly with increasing X-ray energy, the efficiency of a gaseous detector with avalanche amplification, as described above, does not decrease at high X-ray energies.

Secondly, the attenuation coefficient for Compton scattering depends only weakly on the atomic number of the gas. This implies that at high X-ray energies the detector can be operated equally well using a conversion gas with low atomic number, e.g. argon, neon, $CO_2$, methane, ethane, isobuthane, helium etc., with good efficiency also at high X-ray energies.

In a prior art detector using photoelectric absorption in the conversion medium to produce the signal, the position resolution deteriorates with increasing X-ray energy. This is caused by that the liberated photoelectrons are very energetic and can travel a long distance and ionize the conversion medium along the complete trajectory, hence smearing the position resolution.

In the gaseous detector described above, operating through Compton scattering in the conversion medium, the recoil electron has a low kinetic energy also at high X-ray energies, meaning that it can only travel a short distance in the conversion medium. This results in a better position resolution.

It shall be appreciated by the man skilled in the art that the space between the electrodes 23 and 24 may alternatively or complementary be filled with an ionizable liquid or an excitable solid, e.g. a semiconducting material.

The detector device 11 may more generally be any one- or two-dimensional detector, which is capable of discriminating scattered photons to a large extent. The detector may be a gaseous detector or e.g. a solid-state detector.

Figure 5:
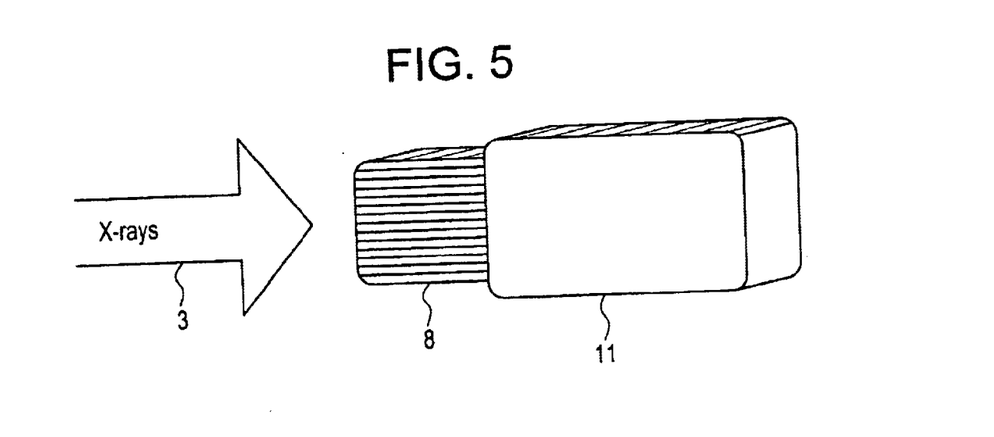
FIG. 5 illustrates schematically, in a perspective view, another embodiment of the detector device for use in the present invention.

With reference finally to FIG. 5 another particular embodiment of the detector device 11 for use in the present invention will be described. This detector device 11 is preferably any of a TFT-based detector; a scintillator-based detector; a solid-state detector such as a CMOS- CCD-, CdZn- or CdZnTe-based detector; a gaseous-based detector; or a combination thereof, for one- or two-dimensional detection of the radiation beam 3 as transmitted through an object under investigation. The detector device is provided with an anti-scatter device 8 for discriminating a large amount of the scattered radiation from being detected as discussed above with reference to FIG. 2.

The anti-scatter device 8 may be a Bucky grid designed for this purpose, i.e. highly scatter-discriminating, wherein a lower transmittance for rays not deflected may be accepted (since the inventive approach with scattered photons creating the image signal lowers the amount of energy deposited within the object to be imaged). In one version the anti-scatter device 8 is provided as a one- or two-dimensional array of radiation-transparent channels arranged in front of the detector device 11.

Scatter suppression may also be achieved by keeping a long distance between the object 7 and the detector 11.

Alternatively, the detector device of FIG. 11 is provided with an anti-scatter mechanism based on dual-detector or dual-energy methods, as described in the above-identified U.S. Pat. No. 6,134,297, and in U.S. Pat. No. 5,649,997 and U.S. Pat. No. 5,771,269, respectively, the contents of which being hereby incorporated by reference.

It shall be appreciated by the man skilled in the art that virtually any kind of detector device and anti-scatter approach known in the art may be employed in the present invention as long as they provide for a high degree of scattering rejection.

What is claimed is:

1. A method for detection of ionizing radiation comprising:

directing ionizing radiation towards an object to be examined;

preventing Compton scattered radiation from being detected; and detecting ionizing radiation spatially resolved as transmitted through said object without being deflected to reveal a spatially resolved density of said object, wherein said ionizing radiation is provided within a spectral range such that more photons of said ionizing radiation are Compton scattered than absorbed through the photoelectric effect in said object to thereby reduce the radiation dose to said object.

2. The method of claim 1 wherein at least 90% of the Compton scattered radiation in said object is prevented from being detected.

3. The method of claim 1 wherein said object is human tissue.

4. The method of claim 3 wherein said human tissue is a breast.

5. The method of claim 3 wherein said ionizing radiation is provided as broadband X-ray radiation between 10 and 300 keV.

6. The method of claim 1 wherein said ionizing radiation is provided as radiation above 30 keV.

7. The method of claim 1 wherein said ionizing radiation is provided within a spectral range, at which photoelectric absorption does not essentially occur in said object.

8. The method of claim 1 wherein said ionizing radiation is provided within a spectral range such that at least two times more photons of said ionizing radiation are Compton scattered than absorbed through the photoelectric effect in said object.

9. The method of claim 1 wherein, the ionizing radiation is spatially resolved based on a first X-ray image, where the first X-ray image illustrates density variations of said object;

a second X-ray image, which illustrates a combination of density and elemental composition variations of said object, is provided; and a third X-ray image, where the elemental composition of said object is deduced from said first and second X-ray images.

10. The method of claim 1 wherein the step of detecting ionizing radiation spatially resolved as transmitted through said object without being deflected is performed by means of a one-dimensional detector including two electrodes, between which an ionizable or excitable substance is located, and a radiation entrance arranged such that said ionizing radiation can enter said detector sideways between the electrodes for ionizing or exciting said substance.

11. The method of claim 10 wherein said ionizable or excitable substance is an ionizable liquid.

12. The method of claim 10 wherein said ionizable or excitable substance is a solid, preferably a semiconductor material.

13. The method of claim 1 wherein the step of detecting ionizing radiation spatially resolved as transmitted through said object without being deflected is performed by means of a one-dimensional gas ionization detector including two electrodes, between which an ionizable gas is located, and a radiation entrance arranged such that said ionizing radiation can enter said detector sideways between the electrodes.

14. The method of claim 13 wherein the step of preventing Compton scattered radiation from being detected is performed by means of keeping a distance between the electrodes short to essentially only allow radiation collimated in a center plane between the electrodes to ionize said gas.

15. The method of claim 13 wherein a distance between the electrodes is kept at least 10 times shorter than the length of the electrodes in the direction of the ionizing radiation as entered.

16. The method of claim 13 wherein a distance between the electrodes is kept below about 2 mm.

17. The method of claim 13 wherein said two electrodes are parallel, and said ionizing radiation is entered into said detector parallel with said two electrodes.

18. The method of claim 13 wherein electrons released as a result of ionization of said ionizable gas by said ionizing radiation entered are avalanche amplified before being detected.

19. The method of claim 18 wherein electrons released as a result of ionization of said ionizable gas by said ionizing radiation and subsequently avalanche amplified are recoil electrons from Compton scattering of said ionizing radiation in said ionizable gas.

20. The method of claim 19 wherein said ionizable gas is a gas or gas mixture of atoms with low atomic number, particularly any of argon, neon, $CO_2$, methane, ethane, isobuthane, helium, or a mixture thereof.

21. The method of claim 13 wherein ionizing radiation as transmitted through said object is entered into said detector sideways between the electrodes without first being collimated by an aperture.

22. The method of claim 13 wherein the step of detecting ionizing radiation spatially resolved as transmitted through said object is performed by means of counting each incident photon of said ionizing radiation.

23. The method of claim 13 wherein the step of detecting ionizing radiation spatially resolved as transmitted through said object is performed by means of integrating charges induced in said gas by said ionizing radiation.

24. The method of claim 1 wherein the step of detecting ionizing radiation spatially resolved as transmitted through said object is performed by means of a detector, wherein the detector is at least one of a TFT-based detector; a scintillator-based detector; a solid state detector such as a CMOS-COD-, CdZn- and CdZnTe-based detector; a gaseous-based detector; and a combination thereof.

25. The method of claim 24 wherein the step of preventing Compton scattered radiation from being detected is performed by means of an anti-scatter device.

26. A method for detection of ionizing radiation comprising:

directing ionizing radiation towards an object to be examined;

preventing radiation originating from pair production in said object from being detected; and detecting ionizing radiation spatially resolved as transmitted through said object without being deflected to reveal a spatially resolved density of said object, wherein said ionizing radiation is provided within a spectral range such that more photons of said ionizing radiation are converted to electrons and positrons in a pair production process than absorbed through the photoelectric effect in said object.

27. The method of claim 26 wherein at least 90% of the radiation originating from pair production in said object is prevented from being detected.

28. An apparatus for radiographic measurement of an object comprising:

an X-ray source, emitting broadband radiation;

a filter arrangement arranged in front of said X-ray source for filtering said emitted broadband radiation;

a source aperture arranged in front of said X-ray source for collimating said emitted broadband radiation;

an object region for housing said object during said radiographic measurement and arranged such that said filtered and collimated broadband radiation can be transmitted through said object; and a detector device arranged to record an image of said filtered and collimated broadband radiation as being transmitted through said object without being deflected, wherein said filter arrangement has a filter function depending on the object to be measured such that said radiation as filtered is within a spectral range such that more X-ray photons are Compton scattered than absorbed through the photoelectric effect in said object; and said detector device is arranged to prevent Compton scattered radiation in said object from being detected.

29. The apparatus of claim 28 wherein said detector device is arranged to prevent at least 90% of the Compton scattered radiation in said object from being detected.

30. The apparatus of claim 28 wherein said object is human tissue.

31. The apparatus of claim 30 wherein said radiation as filtered is within a spectral range of between 10 and 300 keV.

32. The apparatus of claim 28 wherein said radiation as filtered is within a spectral range such that at least two times more photons of said radiation are Compton scattered than absorbed through the photoelectric effect in said object.

33. The apparatus of claim 28 wherein said detector device is a one-dimensional detector including two electrodes, between which an ionizable liquid or an excitable semiconductor is located, and a radiation entrance arranged such that said radiation can enter said detector sideways between the electrodes.

34. The apparatus of any of claims 28 wherein said detector device is a one-dimensional gas ionization detector including two electrodes, between which an ionizable gas is located, and a radiation entrance arranged such that said radiation can enter said detector sideways between the electrodes.

35. The apparatus of claim 34 wherein a distance between the electrodes is short to essentially only allow radiation collimated in a center plane between the electrodes to ionize said gas to thereby prevent Compton scattered radiation from being detected.

36. The apparatus of claim 35 wherein the distance between the electrodes is below about 2 mm.

37. The apparatus of claim 34 wherein said two electrodes are parallel, and said radiation entrance is arranged such that said radiation can enter said detector parallel with said two electrodes.

38. The apparatus of claim 34 wherein said one-dimensional gas ionization detector includes an electron avalanche amplifier for, in said gas, avalanche amplifying electrons released as a result of ionization of said ionizable gas by said radiation.

39. The apparatus of claim 28 wherein said detector device is at least one of a TFT-based detector; a scintillator-based detector; a solid state detector such as CMOS-, CCD-, CdZn- and CdZnTe-based detector; a gaseous-based detector; and a combination thereof, provided with an anti-scatter device.

40. An apparatus for radiographic measurement of an object comprising:

an X-ray source;

a filter arrangement arranged in front of said X-ray source for filtering said emitted broadband radiation;

a source aperture arranged in front of said X-ray source for collimating said emitted broadband radiation;

an object region for housing said object during said radiographic measurement and arranged such that said filtered and collimated broadband radiation can be transmitted through said object; and a detector device arranged to record an image of said filtered and collimated broadband radiation as being transmitted through said object without being deflected, wherein said filter arrangement has a filter function depending on the object to be measured such that said radiation as filtered is within a spectral range such that more X-ray photons are converted to electrons and positrons in a pair production process than absorbed through the photoelectric effect in said object; and said detector device is arranged to prevent radiation originating from pair production in said object from being detected.

41. The apparatus of claim 40 wherein said detector device is arranged to prevent at least 90% of the radiation originating from pair production in said object from being detected.

42. The method of claim 25, wherein the anti-scatter device is an array of radiation-transparent channels arranged in front of said detector.

43. The apparatus of claim 39, wherein the anti-scatter device is a one- or two-dimensional array of radiation-transparent channels arranged in front of said detector.

44. The method according to claim 1, wherein at least 99% of the Compton scattered radiation in said object is prevented from being detected.

45. The method according to claim 1, wherein at least 99.9% of the Compton scattered radiation in said object is prevented from being detected.

46. The method of claim 3, wherein said ionizing radiation is provided as broadband X-ray radiation between 20 and 100 keV.

47. The method of claim 3, wherein said ionizing radiation is provided as broadband X-ray radiation above 30 keV.

48. The method of claim 1, wherein said ionizing is provided within a spectral range such that at least five times more photons of said ionizing radiation are Compton scattered than absorbed through the photoelectric effect in said object.

49. The method of claim 1, wherein said ionizing is provided within a spectral range such that at least ten times more photons of said ionizing radiation are Compton scattered than absorbed through the photoelectric effect in said object.

50. The method of claim 13, wherein a distance between the electrodes is kept at least twenty five times shorter than the length of the electrodes in the direction of the ionizing radiation as entered.

51. The method of claim 13, wherein a distance between the electrodes is kept at least one hundred times shorter than the length of the electrodes in the direction of the ionizing radiation as entered.

52. The method of claim 13, wherein a distance between the electrodes is kept below about 1 mm.

53. The method of claim 13, wherein a distance between the electrodes is kept below about 0.5 mm.

54. The method of claim 13, wherein a distance between the electrodes is kept between about 0.1 mm and 0.5 mm.

55. The method of claim 26 wherein at least 99% of the radiation originating from pair production in said object is prevented from being detected.

56. The method of claim 26 wherein at least 99.9% of the radiation originating from pair production in said object is prevented from being detected.

57. The apparatus of claim 28 wherein said detector device is arranged to prevent at least 99% of the Compton scattered radiation in said object from being detected.

58. The apparatus of claim 28 wherein said detector device is arranged to prevent at least 99.9% of the Compton scattered radiation in said object from being detected.

59. The apparatus of claim 28, wherein said object is breast tissue.

60. The apparatus of claim 30, wherein said radiation as filtered is within a spectral range between 20 and 100 keV.

61. The apparatus of claim 30, wherein said radiation as filtered is within a spectral range above 30 keV.

62. The apparatus of claim 28, wherein said radiation as filtered is within a spectral range such that at least five times more photons of said radiation are Compton scatter than absorbed through the photoelectric effect in said object.

63. The apparatus of claim 28, wherein said radiation as filtered is within a spectral range such that at least ten times more photons of said radiation are Compton scatter than absorbed through the photoelectric effect in said object.

64. The apparatus of claim 35 wherein the distance between the electrodes is below about 1 mm.

65. The apparatus of claim 35 wherein the distance between the electrodes is below about 0.5 mm.

66. The apparatus of claim 35 wherein the distance between the electrodes is between about 0.1 mm and 0.5 mm.

67. The apparatus of claim 40 wherein said detector device is arranged to prevent at least 99% of the radiation originating from pair production in said object from being detected.

68. The apparatus of claim 40 wherein said detector device is arranged to prevent at least 99.9% of the radiation originating from pair production in said object from being detected.

* * * * *